(12) United States Patent
Walters

(10) Patent No.: US 7,824,901 B2
(45) Date of Patent: Nov. 2, 2010

(54) NON-UNIFORM ELECTRIC FIELD CHAMBER FOR CELL FUSION

(75) Inventor: Richard E. Walters, Columbia, MD (US)

(73) Assignee: Cyto Pulse Sciences, Inc., Glen Burnie, MD (US)

( * ) Notice: Subject to any disclaimer, the term of this patent is extended or adjusted under 35 U.S.C. 154(b) by 1169 days.

(21) Appl. No.: 10/580,429

(22) PCT Filed: Dec. 1, 2003

(86) PCT No.: PCT/US03/35982

§ 371 (c)(1), (2), (4) Date: May 24, 2006

(87) PCT Pub. No.: WO2005/066342

PCT Pub. Date: Jul. 21, 2005

(65) Prior Publication Data

US 2007/0105223 A1 May 10, 2007

(51) Int. Cl.
*C12M 3/00* (2006.01)
*C12M 1/34* (2006.01)
(52) U.S. Cl. .................................. 435/288.5
(58) Field of Classification Search .............. 435/288.5
See application file for complete search history.

(56) References Cited

U.S. PATENT DOCUMENTS 4,441,972 A * 4/1984 Pohl ........................ 435/450
4,578,167 A * 3/1986 Schoner ................... 435/450
4,804,450 A * 2/1989 Mochizuki et al. ....... 435/285.2
5,134,070 A * 7/1992 Casnig .................... 435/173.6
2002/0182627 A1 * 12/2002 Wang et al. ................... 435/6
2003/0082163 A1 * 5/2003 Shu ....................... 424/93.21

* cited by examiner

*Primary Examiner*—Walter D Griffin
*Assistant Examiner*—Lydia Edwards
(74) *Attorney, Agent, or Firm*—Marvin S. Towsend

(57) ABSTRACT

An apparatus is provided for carrying out fusion of biological cells (10) and includes a base member (24) on which a conductive outer electrode (18) is supported and has an outer electrode radius (r2) and has an electrode height (19). A conductive inner electrode (20) is supported on the base member (24) and has an inner electrode radius (r1) and also has the electrode height (19). The outer and inner electrodes (18,20) are spaced apart from each other by a gap which defines a fusion chamber (14). The inner electrode radius (r1), the outer electrode radius (r2), and the gap are selected in accordance with a predetermined range of selectable ratios (r1/r2) in a range from 0.7 to 0.9, wherein a selected gap is limited by the range of selectable ratios (r1/r2), and wherein a determined ratio (r1/r2) among the selectable ratios is based on the selected gap, such that compression between the biological cells (10) and permeability between cell membranes are maximized and temperature rise is minimized for providing cell fusion in the fusion chamber (14).

7 Claims, 13 Drawing Sheets

Non Uniform Field Movement

Transmembrane voltage due to Electric field $$Vm = -1.5a|\cos(\theta)|E$$

For coaxial Electrode $$E = -\frac{V}{r_1 \ln(r_1/r_2)}$$

PA-4000 Cyto Pulse Sciences Electroporation System
Cytofusion, 80 µS/cm medium
2 mm cuvette
GAPDH siRNA
PC12 cells Force applied on a neutral particle by a nonlinear electric field $$F_{dep} = a^3 [2\pi \varepsilon_{medium} K(\varepsilon,\sigma,\omega,r)] \nabla E^2$$

a = cell radius
ε = permittivity of medium external to the cell
K = Clausius-Mossotti Function, page 46, Jones
E = Electric field For a coaxial chamber $$\nabla E^2 = -\frac{2V^2}{r_1^3 \ln[(r_1/r_2)^2]}$$

FIG. 8

K562 Cells x K562 cells
Cyto Pulse PA-4000/PA-101 Electrofusion system
Cytofusion medium, 80 µS/cm
6 ml chamber (r1=19.5 mm, r2=23.5 mm, gap = 4 mm)

NON-UNIFORM ELECTRIC FIELD CHAMBER FOR CELL FUSION

TECHNICAL FIELD

The present invention relates generally to methods and apparatus for fusing biological cells to one another. More specifically, the present invention provides methods and apparatus for treating biological cells with electrical fields, such that the biological cells are aligned and have increased cell membrane contact prior to being subjected to cell fusing electric field pulses.

BACKGROUND ART

If a neutrally charged particle, such as a biological cell, is placed in a uniform electric field, such as provided by a pair of same-size planar electrodes, the biological cell does not move toward either one electrode or the other because the attractive forces from both electrodes are the same.

On the other hand, if a neutrally charged biological cell is placed in a non-uniform electric field, such as provided by two electrodes which are both not planar, as shown in PRIOR ART FIG. 1, the biological cell forms a dipole, is attracted to one electrode with greater attractive force than the other, and moves towards the electrode having the greater attractive force.

Such a use of a non-uniform electric field is used in dielectrophoresis, and the concept of using dielectrophoresis to align living cells, followed by a fusion/electroporation pulse, to fuse cells has been in the literature since early 1970's. This process is used to produce hybrids of two different cell types for therapeutic purposes, for hybridoma production for producing monoclonal antibodies, for nuclear fusion, and for producing other hybrid cells.

Dielectrophoresis is the process of applying an electrical force on neutrally charged particles such as living cells. The electrical force causes adjacent living cells to be compressed against one another, as shown in FIG. 5. The force from dielectrophoresis (dielectrophoretic force) results from applying a non-uniform electric field, produced by an electrode pair to which a voltage is applied. The non-uniform electric field separates charges (ions) inside the cells forming a dipole. After the dipole has been formed, the non-uniform electric field then moves the cells towards the highest or lowest electric field intensity. This movement is dependent on the relative conductivities and permittivities of the medium and the biological cells or particles. The living cells are also aligned in the non-uniform electric field, as shown in PRIOR ART FIG. 2.

The dielectrophoretic force is a function of the electric field squared, so electric field polarity is not important. The dielectrophoretic force is also a function of the relative conductivities and permittivities of the medium and the particles or cells. The conductivities and permittivities are a function of the frequency of the applied electric field. Typically, an AC voltage wave, such as a sine wave, is applied across electrodes to produce an alternating electric field. The sine wave voltage, frequency, and duration are optimized for specific cell types.

After the AC wave is applied to align and compress the cells, one or more fusion/electroporation pulses are applied to permeabilize adjacent cell membranes (form pathways between adjacent cell membranes) and to cause cell membranes from both adjacent cells to fuse or commingle. These pathways permit the contents of the cells to mix forming a hybrid fused cell.

Permeabilization is conventionally done in electric fields having uniform electric field intensity so that all cells in the electric field are permeabilized in a uniform manner. The uniform electric field is achieved by using parallel flat plate electrodes.

On the other hand, it is known that permeabilization of all cells in an electric field that has non-uniform electric field intensity would result in the cells being permeabilized in a non-uniform manner. Such non-uniformity in permeabilization is undesirable. Fewer pathways form in the cell membranes resulting in fewer cell fusions.

Following the fusion pulses, another AC field can be applied to hold the cells together while the fused cells stabilize (mature). In some cases, the AC voltage has been linearly increased or decreased to prevent damage to the cells due to a sudden application of a field.

The published PCT International Application No. WO 03/020915 A2 describes AC waveforms that can be applied at a low level to align the cells without creating large forces producing turbulence. After the cells are aligned, the waveform then applied provides a large force which compresses the cells creating a large mutual surface area between the cells just before the permeabilization electric field pulse is applied.

Examples of cell fusion applications include hybridoma production and nuclear transfer. A recent application for electrofusion is to produce therapeutic hybrids for cancer immunotherapy. These hybrids are produced from cancer tumor cells and immune system dendritic cells in an ex vivo process. Each treatment requires a large number of viable hybrids, which results in a new requirement for high efficiency in the hybrid production process. Commercial and clinical uses of these techniques are now important requiring large numbers of hybrid products to be produced in a single batch.

There are a number of techniques (electrical, mechanical, and chemical) available to perform cell fusion. This invention relates to electrical means. The current electric art uses a voltage waveform generator connected to an electrode device or chamber. With respect to known electrical, mechanical, and chemical techniques, the following U.S. patents are of particular interest and are incorporated herein by reference:

U.S. Pat. No. 4,326,934 Apr. 27, 1982 Pohl
U.S. Pat. No. 4,441,972 Apr. 10, 1982 Pohl
U.S. Pat. No. 4,578,168 Mar. 25, 1986 Hofmann
U.S. Pat. No. 4,695,547 Sep. 22, 1987 Hillard
U.S. Pat. No. 4,699,881 Oct. 13, 1987 Matschke et al
U.S. Pat. No. 4,764,473 Aug. 16, 1988 Matschke et al
U.S. Pat. No. 4,784,954 Nov. 15, 1988 Zimmermann
U.S. Pat. No. 4,804,450 Feb. 14, 1989 Mochizuki
U.S. Pat. No. 5,007,995 Apr. 16, 1991 Takahashi
U.S. Pat. No. 5,304,486 Apr. 19, 1994 Chang From the above, it is known to use electrodes or chambers that produce non-uniform electric fields. One such example is two coaxial electrodes forming a chamber. The coaxial chamber was described in detail by Pohl in a book published in 1978. The coaxial chamber was discussed in relation to theoretical dielectrophoresis considerations.

Nevertheless, there has been no description of how to effectively set the dimensions of the coaxial chamber for any particular application. Cell fusion using electrical means requires a non-uniform electric field to align and compress the cells and a uniform electric field to permeabilize the cells. To provide the highest possible efficiency in producing the fused hybrid cells, as required in commercial and clinical applications, the geometric dimensions of the chamber must be carefully selected.

Initially in any cell fusion process one must bring the cells into alignment and contact. In any case, sufficient force must be applied to each cell to overcome the negative surface charge. As stated above, merely applying a uniform electric field will not move a cell because the net charge of the cell is zero. Thus, from the definition of electric field, there is no force applied, because the charge equals zero:

Force=(Electric Field)*(Charge)

However, a non-uniform field induces the positive ions inside each cell to move to one side and the negative ions to move to the opposite side producing a dipole, as shown in PRIOR ART FIG. 1. Once the dipole is induced, because of the presence of a non-uniform electric field, a net force is exerted on the cell because the intensity of the field is greater on one side than the other. The movement of cells in one direction causes the cells to align. Since the cells are now dipoles, the negative side of one cell will attract the positive side of another cell overcoming the negative surface charge, as shown in PRIOR ART FIG. 2. The non-uniform electric field is produced by the electrode device or chamber. The non-uniformity is a function of the electrode configuration, examples of which are shown in PRIOR ART FIGS. 1 and 2.

Generally, the cell types to be fused are placed in a low conductive medium (for example 100 microsemens/cm) to minimize ohmic heating that may harm the cells and that causes turbulence in the medium, thus reducing the number of fused hybrids. In this respect, it would be desirable for biological cells being subjected to cell fusion to be treated so as to reduce heating during cell alignment and cell membrane contact.

The waveform generator has multiple functions. The first function is to produce the AC voltage waveform that is converted into an AC field by the electrode pair or chamber. This AC field brings the cells into alignment/contact. The second function is to compress the cells by briefly increasing the amplitude of the AC waveform. The third function is to produce a pulse voltage that produces an electric field that electroporates the membranes of the cells in close contact, fusing the cells. The fourth function is to apply a low amplitude AC voltage to hold the cells in alignment until the fusion products become viable or stable (mature).

One of the factors for successful fusion is the membrane contact between the adjacent cells. The closer this contact before the fusion pulse is applied, the higher the efficiency of fusion. In U. Zimmermann, et al., "Electric Field-Induced Cell-to-Cell Fusion", J. Membrane Biol. 67, 165-182 (1982), Zimmermann points out that increasing the AC wave electric field strength just before the fusion pulse may be the optimum approach. Clearly, it would be desirable for biological cells that are to undergo cell fusion to be pretreated with pre-fusion non-linear electric field waveforms to produce sufficient force to bring about increased cell membrane contact and then to immediately apply a uniform electric field pulse(s) that permeabilizes the cell membranes in contact, thereby leading to cell fusion.

It would be very desirable to have a chamber that will produce a large number of fused products by applying a large force (proportional to a non-uniform electric field) on the adjacent cells to compress the cells to create a larger surface area between them and then to immediately apply a uniform electric field from one electrode to the next that will permeabilize the largest number of cell membranes in contact.

It is also desirable to have a chamber of sufficient volume to produce a large number of hybrid products.

In view of the above, it would also be desirable to produce a chamber with sufficient uniform and non-uniform electric fields to provide the largest number of fused hybrid cells.

Thus, while the foregoing body of prior art indicates it to be well known to use coaxial chambers, the prior art described above does not teach or suggest a method to determine how to select the chamber geometry which has the following combination of desirable features: (1) provides sufficient force (non-uniform field intensity) to compress the cells providing a large membrane contact area without excessive heating; (2) provides sufficient uniform field intensity to permeabilize the cells; and (3) produces a large number of hybrid products. The foregoing desired characteristics are provided by the unique coaxial cell fusion chamber of the present invention as will be made apparent from the following description thereof. Other advantages of the present invention over the prior art also will be rendered evident.

Additional U.S. patents and published U.S. patent applications that are of interest include:
  U.S. Pat. No. 4,561,961 Dec. 31, 1985 Hofmann
  U.S. Pat. No. 5,001,056 Mar. 19, 1991 Snyder et al
  U.S. Pat. No. 5,589,047 Dec. 31, 1996 Coster et al
  U.S. Pat. No. 5,650,305 Jul. 22, 1997 Hui et al
  US2003/0082163, May 1, 2003 Shu
  Additional literature references include:
1. R. Bischoff, et al., "Human Hybridoma Cells Produced by Electro-Fusion", Fed. Eur. Biochem. Soc. Lett. 147, 64-68 (1982).
2. L. Changben, et al., "Use of Human Erythrocyte Ghosts for Transfer of 125.sub.I-BSA and 125.sub.I-DNA into Animal Cells from Cell Fusion", Scientia Sinica (Series B) 25, 680-865 (1982).
3. C. S. Chen, et al., "Biological Dielectrophoresis: The Behavior of Lone Cells in a Non-uniform Electric Field", Ann. N.Y. Acad. Sci. 238, 176-185 (1974).
4. Coster, H. G. L. and Zimmermann, U. "Direct Demonstration of Dielectric Breakdown in the Membranes of Valonia utricularis." Zeitschrift fur Naturforschung. 30 c, 77-79.1975.
5. Coster, H. G. L. and Zimmermann, U. "Dielectric Breakdown in the Membranes of Valonia utricularis: the role of energy dissipation". Biochimica et Biophysica Acta. 382, 410-418,1975.
6. Coster, H. G. L. and Zimmermann, U. "The mechanisms of Electrical Breakdown in the Membranes of Valonia utricularis." Journal of Membrane Biology. 22, 73-90,1975.
7. K. Kaler, et al., "Dynamic Dielectrophoretic Levitation of Living Individual Cells", J. Biol. Phys. 8, 18-31 (1980).
8. A. R. Murch, et al., "Direct Evidence that Inflammatory Multi-Nucleate Giant Cells Form by Fusion", Pathol. Soc. Gr. Brit. Ire. 137, 177-180 (1982).
9. Neumann, B et al. "Cell Fusion Induced by High Electrical Impulses Applied to Dictyostelium", Naturwissenschaften 67, 414, 1980
10. Petrucci, General Chemistry: Principles and Modern Applications, 4th ed., p. 621, 1985 (no month).
11. Zimmermann et al., Electric Field-Induced Cell-to-Cell Fusion, The Journal of Membrane Biology, vol. 67, pp. 165-182 (1982) [no month].
12. Pohl, H. "Dielectrophoresis", Cambridge University Press, 1978.
13. H. A. Pohl, "Biophysical Aspects of Dielectrophoresis", J. Biol. Phys. 1, 1-16 (1973).
14. H. A. Pohl, et al., "Continuous Dielectrophoretic Separation of Cell Mixtures", Cell Biophys. 1, 15-28 (1979).
15. H. A. Pohl, et al., "Dielectrophoretic Force", J. Biol. Phys. 6, 133 (1978).
16. H. A. Pohl, et al., "The Continuous Positive and Negative Dielectrophoresis of Microorganisms", J. Bio. Phys. 9, 67-86 (1981).

17. Sale, J. H. and Hamilton, W. A. "Effects of High Electric Fields on Micro-Organisms", Biochimica et Biophysica Acta. 163, 37-43, 1968.
18. Sepersu, E. H., Kinosita, K. and Tsong, T. Y. "Reversible and Irreversible Modification of Erythrocyte Membrane Permeability by Electric Fields" Biochimica et Biophysica Acta. 812, 779-785, 1985.
19. J. Vienken, et al., "Electric Field-Induced Fusion: Electro-Hydraulic Procedure for Production of Heterokaryon Cells in High Yield", Fed. Eur. Biomed. Soc. Lett. 137, 11-13 (1982).
20. H. Weber, et al., "Enhancement of Yeast Protoplast Fusion by Electric Field Effects", A Preprint for Proceedings of the Fifth International Symposium on Yeasts, London, Ontario, Canada, Jul. 80.
21. Zimmermann, U. "Electrical Field Mediated Fusion and Related Electrical Phenomena", Biochimica et Biophysica Acta. 694, 227-277. 1982.
22. Zimmermann, U. et al "Fusion of Avena Sativa Mesophyll Proptoplasts by Electrical Breakdown", Biochimica et Biophysica Acta. 641, 160-165, 1981. 1982.
23. U. Zimmermann, et al., "Electric Field-Induced Release of Chloroplasts from Plant Protoplasts", Naturwissen 69, 451 (1982).
24. U. Zimmermann, et al., "Electric Field-Mediated Cell Fusion", J. Biol. Phys. 10, 43-50 (1982).
25. U. Zimmermann, "Cells with Manipulated Functions: New Perspectives for Cell Biology, Medicine, and Technology", Angew. Chem. Int. Ed. Engl. 20, 325-344 (1981).
26. Electromechanics of Particles, Thomas B. Jones, 1995, Cambridge University Press.
27. Electroporation and Electrofusion in Cell Biology, Eberhard Neumann, Arthur E. Sowers, and Carol A. Jordon, Plenum Press, New York 1989.

As explained below with respect to the subject invention, prior art ratios r1/r2 and gaps of known prior art chambers are outside the respective ranges of the subject invention. Such prior art are as follows:
1. Dielectricophoresis of cell size liposomes, 13 December 1993. r1/r2=0.25, gap=0.75 mm.
2. Hofmann U.S. Pat. No. 4,578,168, Mar. 25, 1986, r1/r2=0.139, gap=0.155 mm.
3. Hillard U.S. Pat. No. 4,695,547, Sep. 22, 1987, r1/r=0.162, gap=13 mm
4. Matschke U.S. Pat. No. 4,699,881, Oct. 13, 1987, r1/r2=0.98, gap=0.4 mm.
5. Zimmerman U.S. Pat. No. 4,764,473, Aug. 16, 1988, no dimensions.
6. Mochizuki, U.S. Pat. No. 4,804,450, Feb. 14, 1989, r1/r2=0.962, gap=2 mm.
7. Takahashi, U.S. Pat. No. 5,007,995, Apr. 16, 1991, r1/r2=0.263, gap=2.8 mm
8. Chang, U.S. Pat. No. 5,304,486, Apr. 19, 1994, r1/r2 not given, gap=0.5 to 2.0 mm
9. Shu, US2003/0082163, May 1, 2003, r1/r2 not given, gap 2 to 5 mm.

DISCLOSURE OF INVENTION

The present invention provides an apparatus for carrying out fusion of biological cells and includes: an inner electrode having a first electrode radius (r1) and an electrode height and an outer electrode having a second electrode radius (r2) and the same electrode height. The inner electrode and the outer electrode are concentric. A gap is provided between the inner electrode and the outer electrode, and the size of the gap is the difference between the second electrode radius and the first electrode radius. A cell fusion volume is defined by the electrode height, the gap, the first electrode radius, and the second electrode radius. The first electrode radius, the second electrode radius, and the gap are selected in accordance with a predetermined range of selectable ratios (r1/r2) of the first electrode radius to the second electrode radius, wherein the range of selectable ratios (r1/r2) is from 0.7 to 0.9, wherein a selected gap limited by the range of selectable ratios (r1/r2), and wherein a determined ratio (r1/r2) of the selectable ratios is based on the selected gap, such that compression between the biological cells and permeability between cell membranes are maximized and temperature rise is minimized for providing cell fusion in the cell fusion volume.

It is understood, that both the inner electrode and the outer electrode are provided with means for connecting with cables or other electrical conductors coming from a an electrical waveform generator.

As discussed further below in greater detail, as the ratio r1/r2 would be less than 0.7, the Percent Change in Electric Field Intensity would be greater than 30%, which would result in undesirably low cell permeabilization and undesirably low cell fusion.

In addition, as the ratio r1/r2 would be greater than 0.9, the electric field intensity would become very uniform, which would result in a very low compressive force for a fixed AC voltage. This would result in low cell fusion. If to compensate, the AC voltage would be increased to maintain a constant compressive force, undesirable heating of the medium would occur which would cause an undesirable temperature rise which would kill the cells.

With the present invention the geometric parameters of a coaxial chamber may be selected to produce a chamber which will simultaneously provide cell compression and permeabilization without excessive heating to produce large numbers of fused hybrid cells.

All of the prior art that provided sufficient information to determine the chamber parameters were either well below or well above the preferred parameters of this invention. All were very small volumes, less than a few hundred microliters (in contrast with the subject invention which is scalable up to many milliliters), and none considered the trade-off between compressive force and permeabilization (which the principles of the subject invention teach).

In accordance with another aspect of the invention, a method is provided for selecting an inner electrode, an outer electrode, and a gap between the inner electrode and the outer electrode for a cell fusion chamber for fusing biological cells. The method includes the steps of:

determining two of a first electrode radius of the inner electrode, a second electrode radius of the outer electrode, and the gap between the inner electrode and the outer electrode;

setting the ratio of the first electrode radius to the second electrode radius to a value in a range between 0.7 to 0.9; and calculating the third of the first electrode radius of the inner electrode, the second electrode radius of the outer electrode, and the gap between the inner electrode and the outer electrode, such that compression between the biological cells and permeability between cell membranes are maximized and temperature rise is minimized for providing cell fusion in the cell fusion chamber.

More specifically, with the method, the ratio of the first electrode radius to the second electrode radius is set to a value in a range between 0.80 to 0.85, and the gap is in a range of 2 to 10 millimeters for cell radius between 2 and 10 microns.

With further consideration of the concept of scalability, with the subject invention, volume of the cell fusion chamber can be increased by simple increasing the electrode height and keeping the ratio r1/r2 and the gap constant. In addition, by simply increasing the electrode height and keeping r1/r2 constant, temperature in the medium does not change.

BRIEF DESCRIPTION OF DRAWINGS

The invention will be better understood and the above objects as well as objects other than those set forth above will become more apparent after a study of the following detailed description thereof. Such description makes reference to the annexed drawing wherein:

FIG. 8 shows the equation for dielectrophoretic force applied to a neutral cell by a non-uniform electric field. Also shown is the equation for the non-uniform electric field intensity for a coaxial chamber.

FIG. 11A is for a 2 micron cell radius; FIG. 11B is for a 6 micron cell radius; and FIG. 11C is for a 10 micron cell radius.

FIG. 12A is for a 2 micron cell radius; FIG. 12B is for a 6 micron cell radius; and FIG. 12C is for a 10 micron cell radius.

MODES FOR CARRYING OUT THE INVENTION

Figure 1:
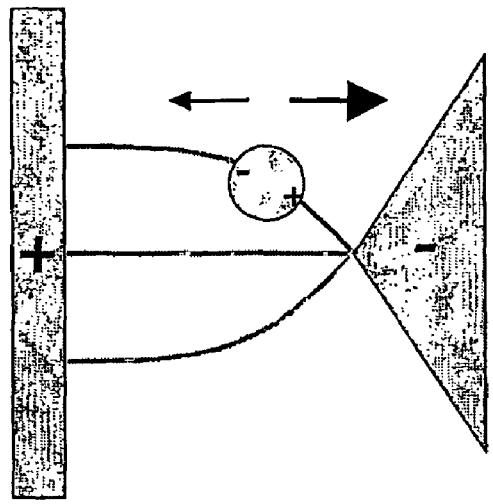
FIG. 1 illustrates PRIOR ART dipole formation in biological cells under the influence of a non-uniform electric field created by non-symmetrical electrodes.
Figure 2:
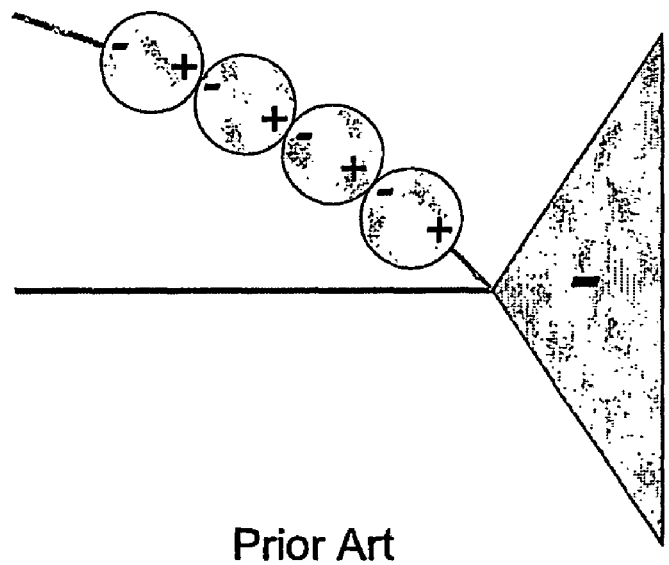
FIG. 2 illustrates a PRIOR ART path of movement of biological cell in a non-uniform electric field created by non-symmetrical electrodes and also illustrates pearl chain alignment and formation of biological cells.
Figure 3:
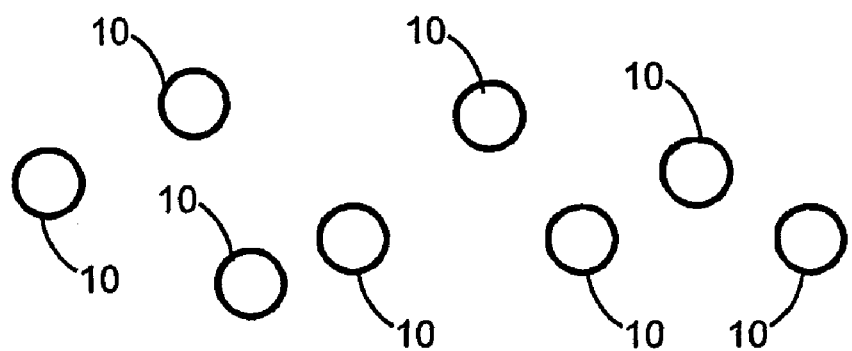
FIG. 3 shows independent biological cells 10 prior to applying a relatively low amplitude, long duration pre-fusion electric field waveform.
Figure 4:
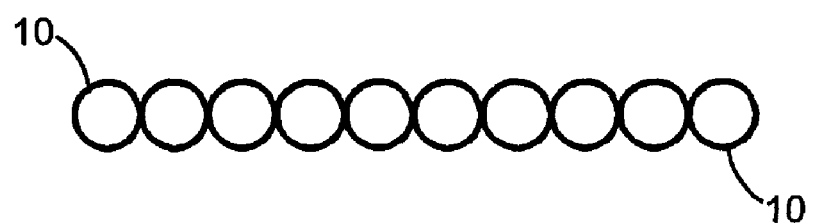
FIG. 4 shows tangentially contacting biological cells 10 in pearl chain alignment during application of a relatively low amplitude, long duration pre-fusion electric field waveform.
Figure 5:
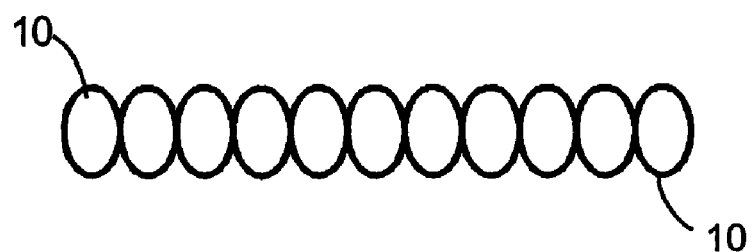
FIG. 5 shows closely contacting and compressed biological cells 10 during application of a relatively high amplitude, short duration pre-fusion electric field waveform, following the application of the relatively low amplitude, long duration pre-fusion electric field waveform that was applied in FIG. 4.
Figure 6:
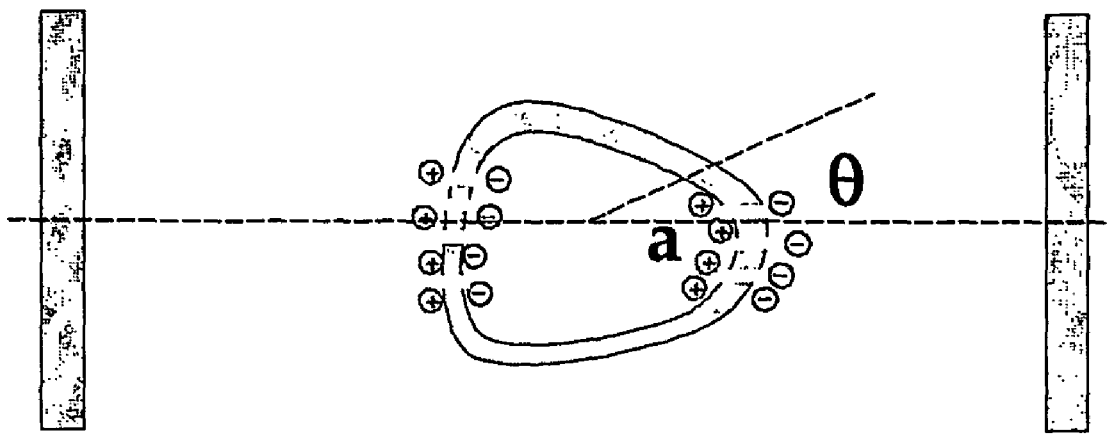
FIG. 6 shows the equation for transmembrane voltage (TMV) induced by the application of an electric field. Also shown is the electric field equation of a coaxial chamber. The critical point of onset of permeabilization occurs with a TMV between approximately 0.5 and 1.5 volts. The desirable electric field intensity for cell fusion is larger than the electric field intensity required for onset of permeabilization.

The cell membrane is permeabilized by the application of an electric field. The equation is presented and illustrated in PRIOR ART FIG. 6. The permeabilization is directly proportional to the electric field intensity.

Figure 15:
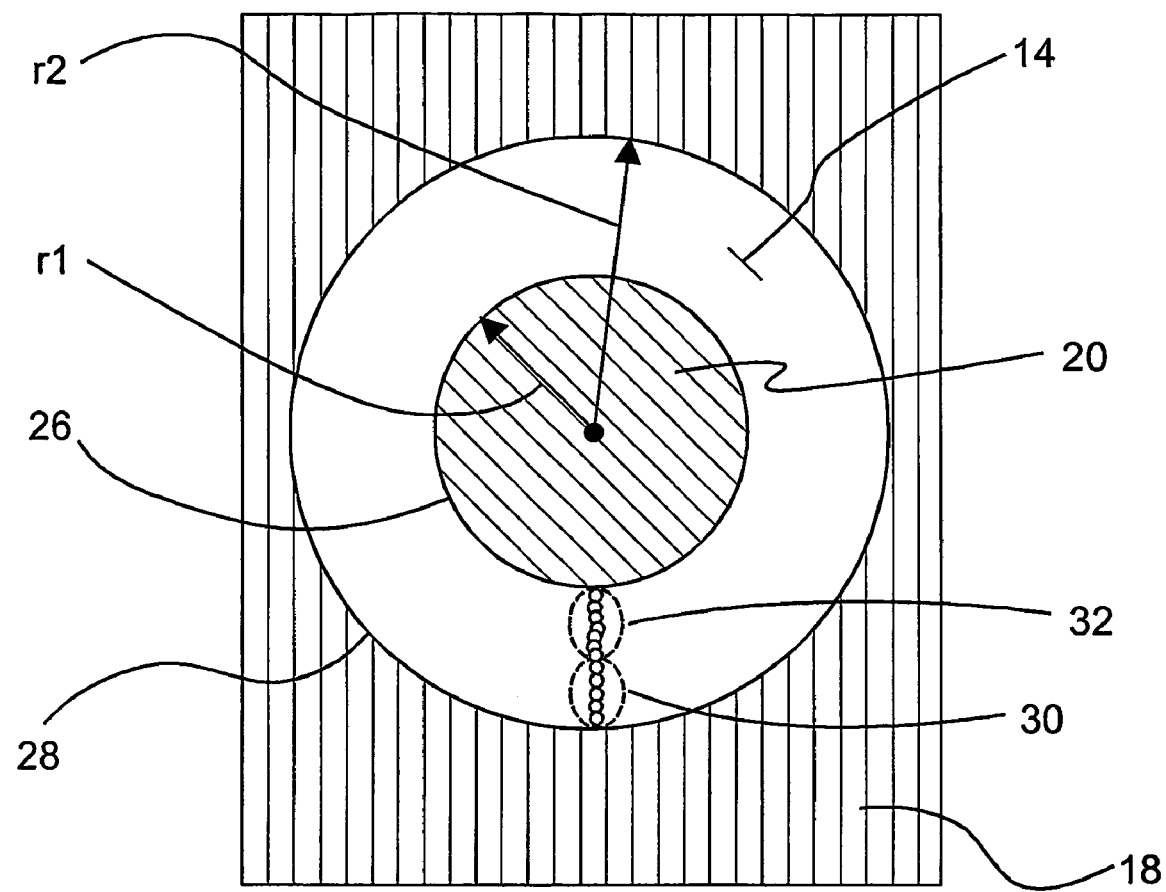
FIG. 15 shows an area of more intense electric fields close to the inner electrode and an area of less intense electric field close to the outer electrode.

Coaxial cell fusion chambers produce electric fields having non-uniform electric field intensity, and as mentioned above, electric fields having non-uniform electric field intensity result in non-uniform permeabilization. As shown in FIG. 15, the area 32 of more intense electric field intensity with greater permeabilization is closer to inner electrode 20, and the area 30 of less intense electric field intensity with lesser permeabilization is closer to outer electrode 18. Referring back to the electric field formula for a coaxial chamber in FIG. 6, as the ratio of r1/r2 decreases, the intensity of the electric field becomes more non-uniform. Referring again to FIG. 15, r1 is the radius of the inner electrode 20; and r2 is the radius of the outer electrode 18.

For purposes of the present invention, the percent change of the electric field intensity (Percent Change) from one electrode to the second coaxial electrode is defined as:

Percent Change=100*[$E$(at inner)−$E$(at outer)]/$E$(at inner)

=100*(1−r1/r2) where (r2>r1)

where r1 is the radius of the inner electrode, and r2 is the radius of the outer electrode.

The percent change in electric field intensity from the inner to the outer electrode is only a function of the ratio of r1/r2, and is independent of gap (G).

The electrode gap is defined as:

Gap=r2−r1

The dimensions of the coaxial chamber are uniquely defined by either r1/r2, gap, and electrode height or by r1, r2, and electrode height. The electric field is most intense at the inner electrode and least intense at the outer electrode. As the gap decreases, the ratio r1/r2 approaches "one", and the more uniform (or less non-uniform) the electric field changes from inner electrode to outer electrode. Stated somewhat differently, the herein-defined "Percent Change in Electric Field Intensity" is a measure of the non-uniformity of the electric field intensity.

Figure 7:
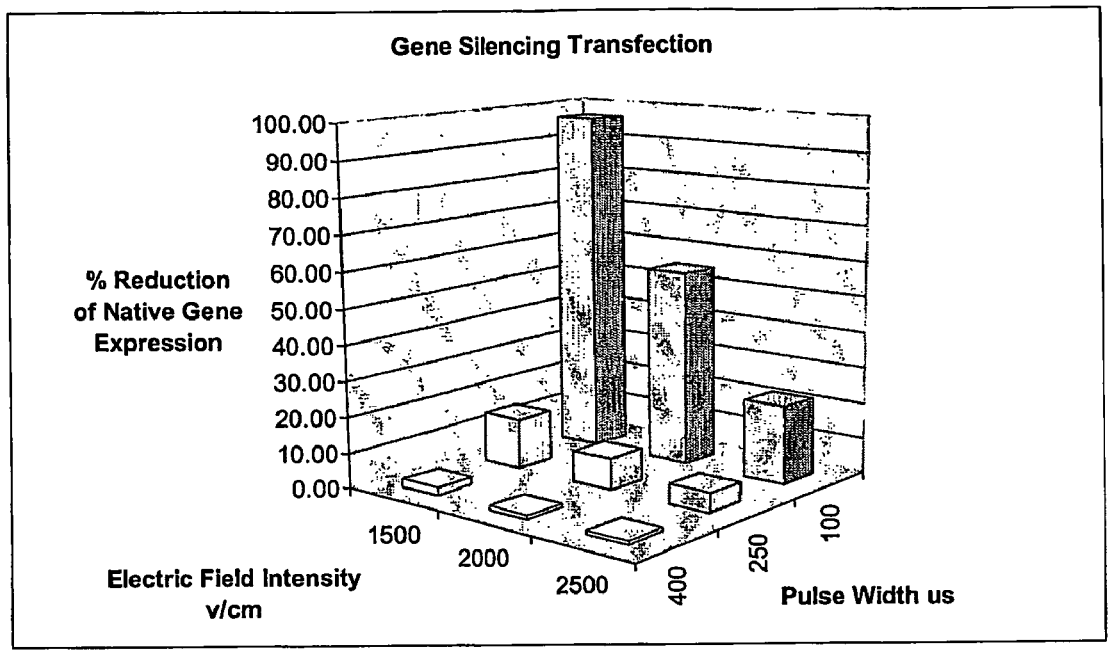
FIG. 7 relates to gene silencing using siRNA (small interfering RNA) being delivered into biological cells, wherein reduction on % expression of the gene is dependent upon the efficiency of cell permeabilization, which is also an essential step in cell fusion.

A relevant question is just how non-uniform an electric field from inner electrode to outer electrode should the electric field be to permeabilize the largest number of cells in the gap? An answer to this question can be found in a study of FIG. 7 wherein an examination of siRNA transfection data provides an example. Although transfection does not involve cell fusion, transfection is dependent upon cell membrane permeabilization as is cell fusion. More specifically, siRNA transfection must deliver only through the cell membrane and not into the nucleus so this transfection data is representative of the membrane permeabilization required in cell fusion.

FIG. 7 relates to gene silencing using siRNA (small interfering RNA) being delivered into biological cells, wherein reduction of percent expression of the native gene is dependent upon the efficiency of cell membrane permeability, which is also an essential step in cell fusion. This is a model for cell permeabilization. The siRNA works by causing destruction of targeted RNA thereby silencing the effect of a gene expression. This produces a reduction of native gene expression as more siRNA is delivered. It is a good model for cell permeabilization because its effects occur in the cytoplasm, and that is where permeabilization using electric fields (electroporation and electrofusion) delivers material. In contrast, delivery of genes using plasmids (another potential model) requires movement of DNA to the nucleus and this becomes a second order effect not directly related to the degree of permeabilization. It is important to note that the electric field based permeabilization used for electroporation is the same as that used for electrofusion.

For example in FIG. 7 there is a 25% change (increase) in electric field intensity from 1500 V/cm to 2000 V/cm (100×(2000−1500)/2000). In addition, over the same interval, there is an approximately 42% (95%−53%)change (decrease) in percent expression (by implication a 42% increase in cell membrane permeabilization). While this example is a property of the specific cell type and material, it is still quite dramatic. By extrapolation, approximately a 10% increase in electric field intensity resulted in approximately 15% increase in delivery efficiency as shown by a reduction of native gene expression (by implication an increase in cell membrane permeabilization).

Clearly, from the above example, it can be concluded that great care must be taken in selecting parameters (r1/r2 and gap) to minimize the non-uniformity of the non-uniform electric field intensity to achieve desirable cell membrane permeability among the complete cell population for cell fusion.

In contrast to permeabilization, the dielectrophoretic force on a cell (important in cell alignment and compression discussed above) is given by the equation presented and illustrated in FIG. 8. This equation from Pohl and Jones has four elements of interest. The force is proportional to:

1. The cube of the cell radius
2. The permittivity of the medium external to the cells.
3. K which is the Clausius-Mossotti function.
4. The del of the electric field squared.

The cube of the cell radius and the permittivity of the medium external to the cells need no further explanation.

Figure 9A:
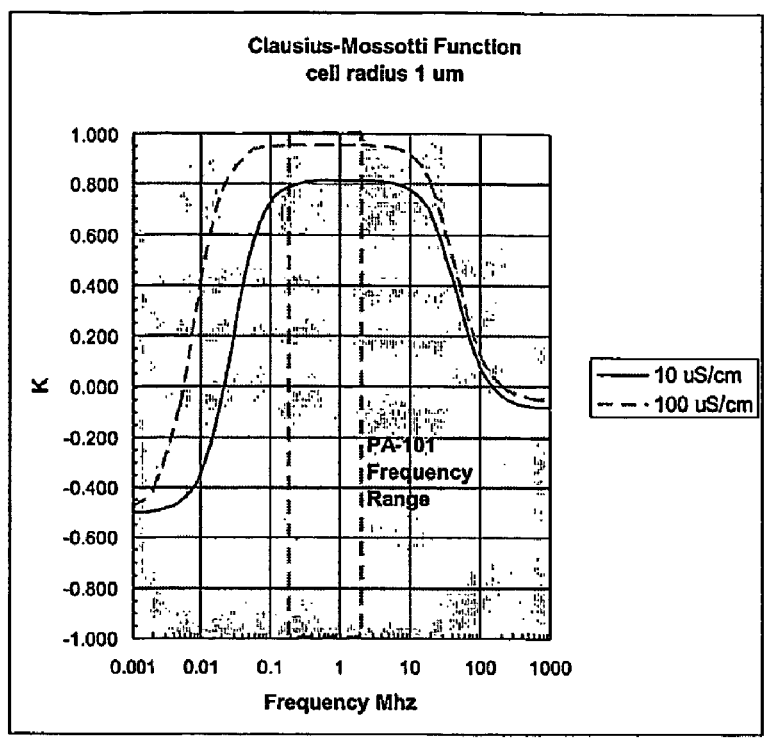
FIG. 9A shows the Clausius-Mossotti Function for a cell diameter of 1 micron.
Figure 9B:
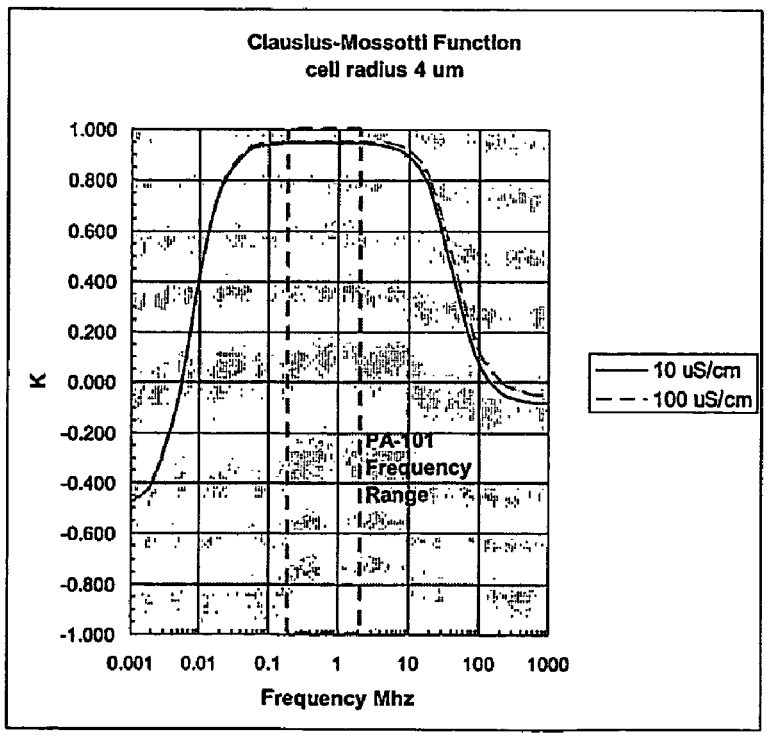
FIG. 9B shows the Clausius-Mossotti Function for a cell diameter of 4 microns.

The Clausius-Mossotti function is illustrated in FIG. 9A and FIG. 9B. It is a function of the permittivity of the medium and the conductivity inside and outside the cell. The examples presented are for an external conductivity of 10 microS/cm (in solid lines) and an external conductivity of 100 microS/cm (in broken lines). The Clausius-Mossotti function changes with frequency. At DC and at lower AC frequencies, the function is negative; this means the force on a cell is toward the outer electrode. In the frequency range 0.2 to 2 MHz, the function is positive, and the force on the cell is towards the inner electrode. This is the preferred mode of operation. K is approximately 0.95 at 100 microS/cm external medium conductivity and cell radius greater than 4 micrometers. In view of the above, the Clausius-Mossotti function is not factor in coaxial chamber geometry for cell radius greater than 4 microns and external medium with conductivity greater than 100 microS/cm The Electric Field Function $delE^2$ is solely a function of coaxial chamber geometry. The Electric Field Function implies a differential (first derivative) of the electric field squared. If the electric field is uniform, the Electric Field Function is zero, and there is no force on the cell.

As in the case of the electric field intensity, the present invention also defines percent change in the force as the Percent Change in the Electric Field Function. This equation is:

Percent Change in $delE^2 = [1-(r1/r2)^3]*100$

As with the above-mentioned Percent Change in Electric Field Intensity, the Percent Change in the Electric Field Function is also related to just the ratio r1/r2.

From the herein defined Percent Change in Electric Field and the herein defined Percent Change in Electric Field Function, it appears that the smaller ratio r1/r2, the smaller the percent change in both. In addition, the Electric Field function ($delE^{2)}$) has a second characteristic, as the ratio r1/r2 approaches one, the absolute magnitude of $delE^2$ approaches zero.

In summary, here are two opposing considerations:
1. As the ratio r1/r2 approaches one, the electric field intensity becomes more uniform, which is desirable for cell permeabilization.
2. As the ratio r1/r2 approaches zero, the force on the cell increases, which is desirable for cell alignment and compression.

Following the principles of the present invention, one can readily select a ratio of r1/r2 that is a best compromise to select the geometric dimensions of the cell fusion chamber for cell permeabilization and cell alignment and compression.

In order to select coaxial electrode parameters (r1/r2 and gap) to provide for an adequate compressive force, the magnitude of an adequate compressive force needs to be determined. To determine the magnitude of that force, the $F_{dep}$ equation (in FIG. 8) was used with two sets of empirical data. The results are in Table I below.

TABLE I

| Cell Type | Approx Radius | R1 mm | r2 mm | AC Amp v-pk | AC Dur seconds | Force nanodynes |
|---|---|---|---|---|---|---|
| K562 | 7 micron | 19.5 | 23.5 | 70 | 15 | 0.240 |
| A549 | 7 micron | 19.5 | 23.5 | 75 | 10 | 0.270 |

Figure 10:
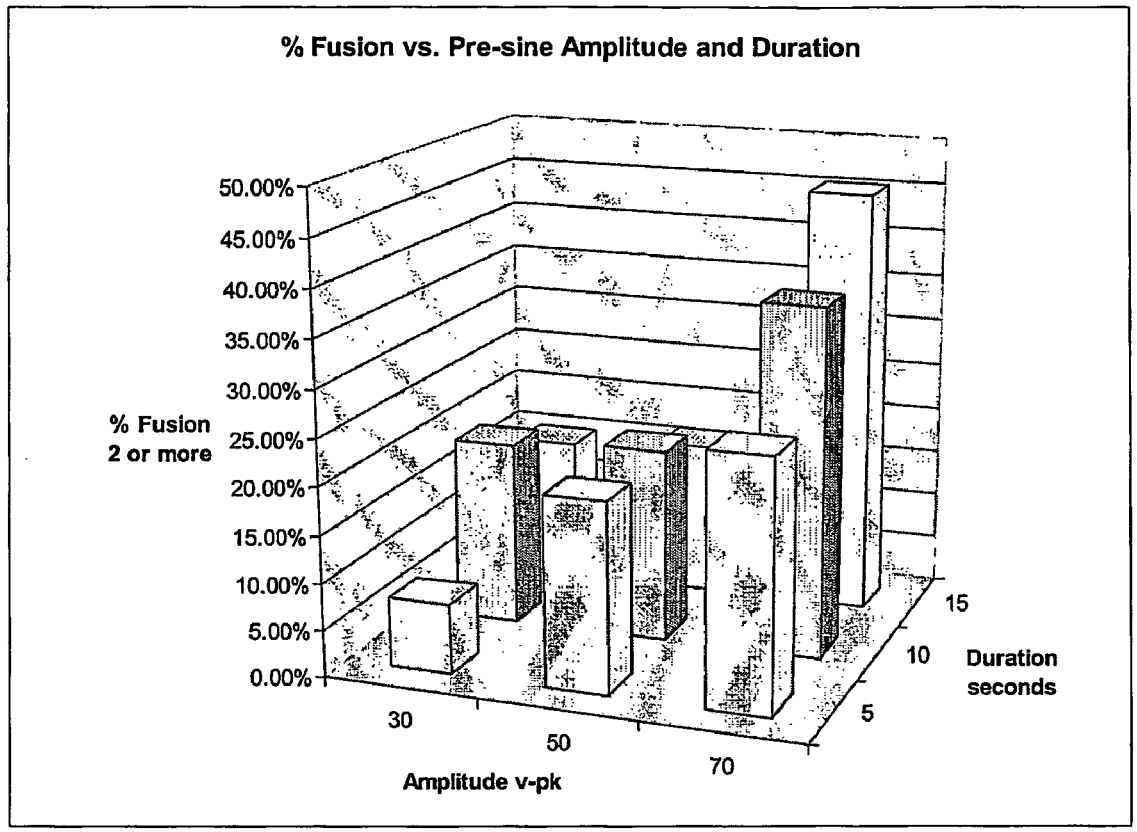
FIG. 10 shows the percent auto fusion of K562 cells versus applied AC voltage and AC voltage duration.

Both of these protocols resulted in a maximum number of cell fusion hybrids for the cells and medium used. The K562 self fusion experiments were done at Cyto Pulse, Inc., Hanover, Md., USA, see FIG. 10. The A549 self fusion experiments were done at the Arizona Cancer Center (AZCC) and presented by poster at the American Association of Cancer Researchers (AACR) in April 2002. The AZCC/AACR data used lower AC voltage to align and higher voltage AC to compress. Only the compression data is included in the table above. The Cyto Pulse PA-4000/PA-101 cell fusion system and a 6 ml chamber (with r1/r2 equaling 0.83) were used in both experiments. In summary, the compression force for these cells was in the 0.1 to 1.0 nanodyne range The optimum dimensions of the ratio r1/r2 and the gap for a coaxial electrode are determined by the parameters and their respective characteristics as set forth in Table II below.

TABLE II

| Parameter | Characteristic |
|---|---|
| Cell radius | Determined by cell type |
| Relative permittivities of external medium | About 75 for most low conductivity mediums |
| Ratio r1/r2 | Greater than or equal to 0.7 |

TABLE II-continued

| Parameter | Characteristic |
| --- | --- |
| K (Clausius-Mossotti) | 0.95 |
| Force | A good starting point is 1 nanodyne |
| AC voltage in volts rms | Calculated from FIG. 8 |
| AC duration in seconds | Generally between 5 and 20 |

To find the optimum dimensional values for the above conditions, the ratio r1/r2 and the gap are used as parameters with 1 nanodyne as a starting point. As ratio r1/r2 approaches one, the AC voltage required to produce the required force gets very large. The high voltage AC wave that is applied for many seconds will very rapidly heat the medium in the electrode and destroy the cells.

Figure 11A:
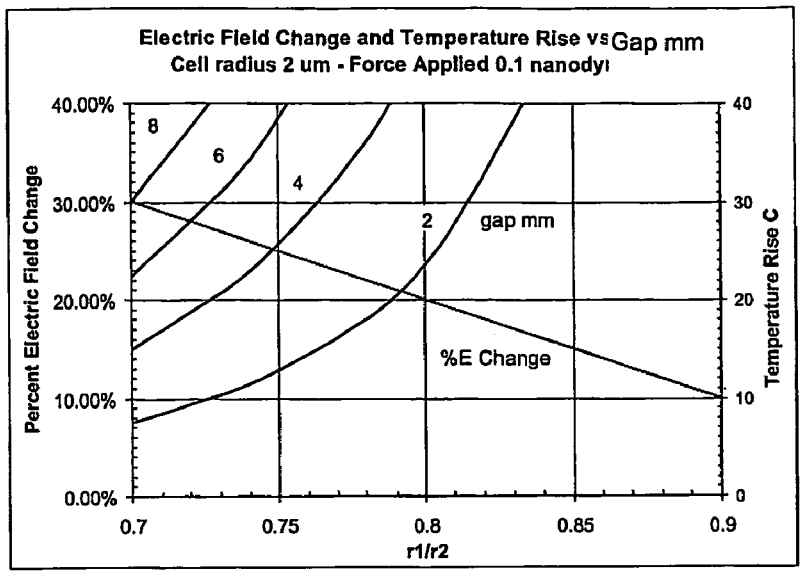
FIGS. 11A, 11B, and 11C show Percent Electric Field Change and Temperature Rise as a function of ratio r1/r2 for 0.1 nanodyne of compressive force between the biological cells. More specifically.
Figure 11B:
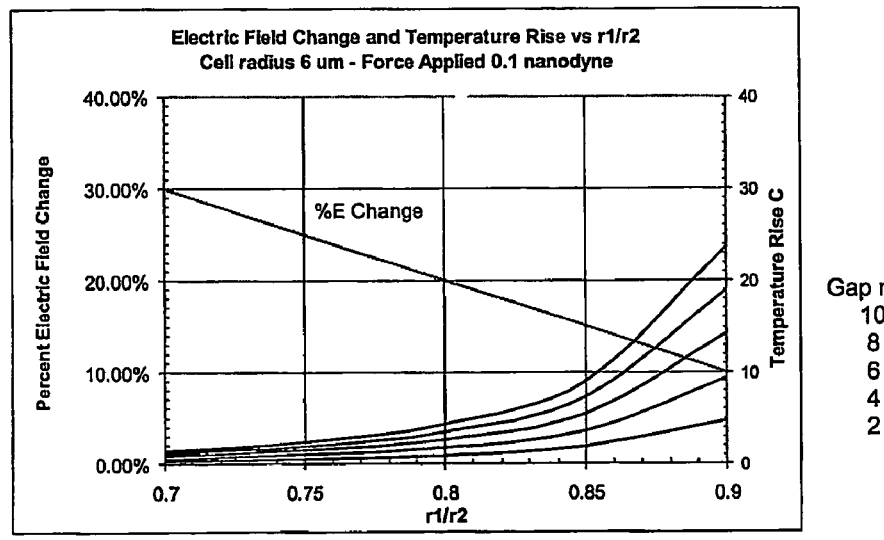
Figure 11C:
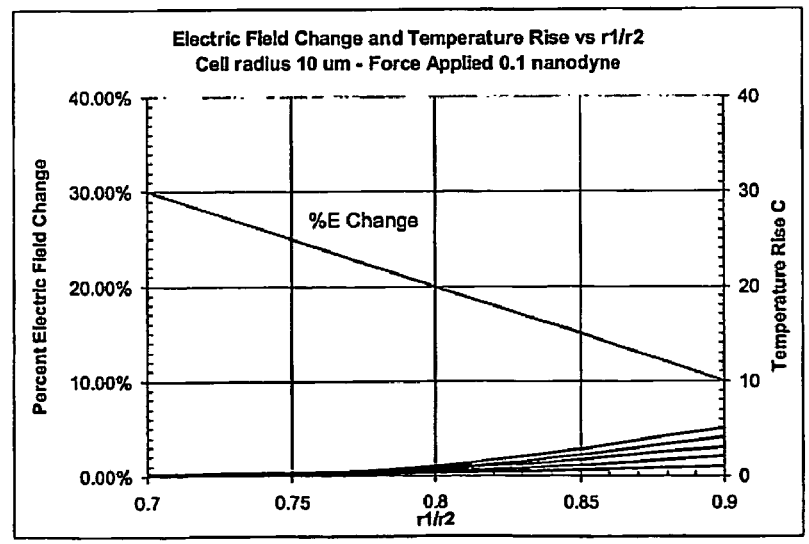
Figure 12A:
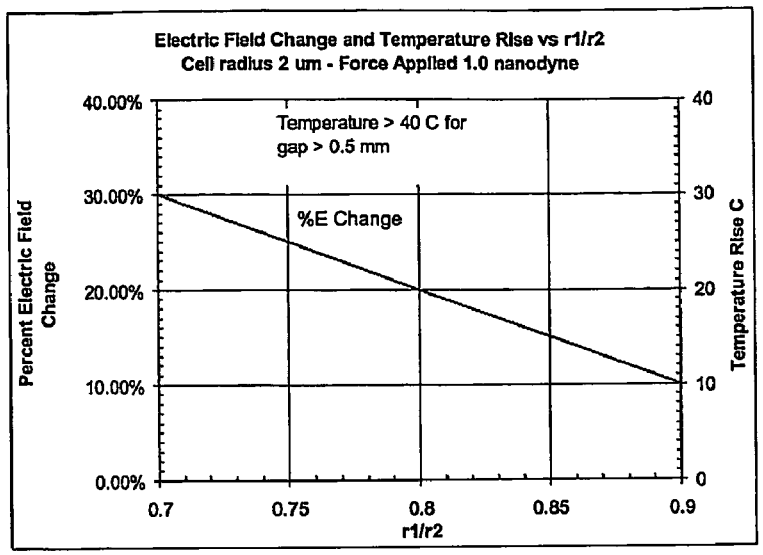
FIGS. 12A, 12B, and 12C show Percent Electric Field Change and Temperature Rise as a function of ratio r1/r2 for 1.0 nanodyne compressive force between biological cells. More specifically.
Figure 12B:
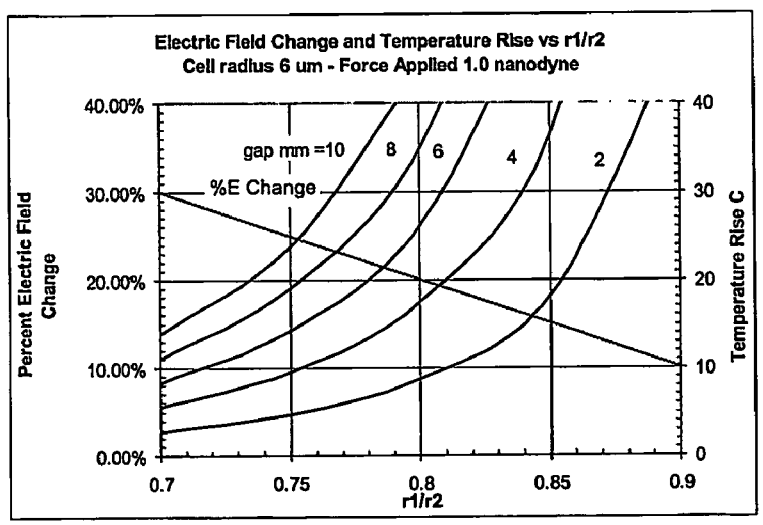
Figure 12C:
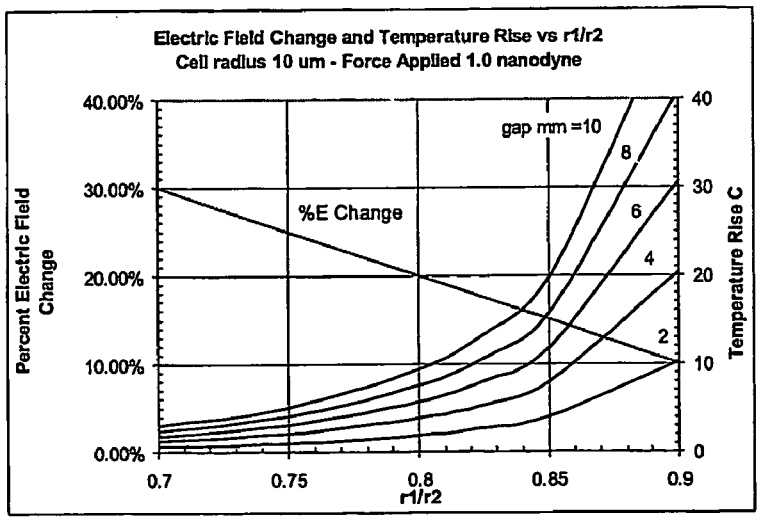

Two sets of examples have been calculated. One set of examples has been calculated for a force of 0.1 nanodyne, as shown in FIGS. 11A, 11B, and 11C. A second set of examples has been calculated for a force of 1.0 nanodyne, as shown in FIGS. 12A, 12B, and 12C. For both sets of examples, selectable ratios r1/r2 from 0.7 to 0.9 and gaps from 2 to 10 mm are presented.

For 0.1 nanodyne, FIG. 11A is for a cell radius of 2 microns. FIG. 11B is for a cell radius of 6 microns. FIG. 11C is for a cell radius of 10 microns.

For 1.0 nanodyne, FIG. 12A is for a cell radius of 2 microns. FIG. 12B is for a cell radius of 6 microns. FIG. 12C is for a cell radius of 10 microns.

As shown in FIG. 12A, for a cell radius of 2 microns, the AC voltage required was so high that heating was above 40 deg. C. for all realistic gap values. This may be somewhat compensated for by cooling the chamber. As shown in FIGS. 12B and 12C, significant heating still occurs for a radius of 6 microns and 10 microns, respectively. Some of the excess heating may be compensated for by external cooling. Operating with a ratio r1/r2 at above 0.9, the temperature increase in the medium is so significant that it is not a desirable operating range for cell radius of 10 microns or less.

For FIGS. 11A and 11B, the medium heating is less and chamber cooling is an option to reduce heating.

In the case of particles or biological cells having cell radiuses greater than 10 microns, lower AC voltages are required, and very small ratio r1/r2 are possible.

In the mid range which contains cell radiuses of most tumor and immune system cells, careful consideration must be given. Generally a ratio r1/r2 of 0.8 to 0.85 should be used with gaps in the range of 2 to 10 mm. One of the Cyto Pulse 6 ml experimental chambers has a ratio r1/r2 of 0.83 and a gap of 4 mm. The use of this electrode with various cell types for hybridoma production and cancer-immune cell therapeutic hybrid production has resulted in good efficiencies.

Figure 13A:
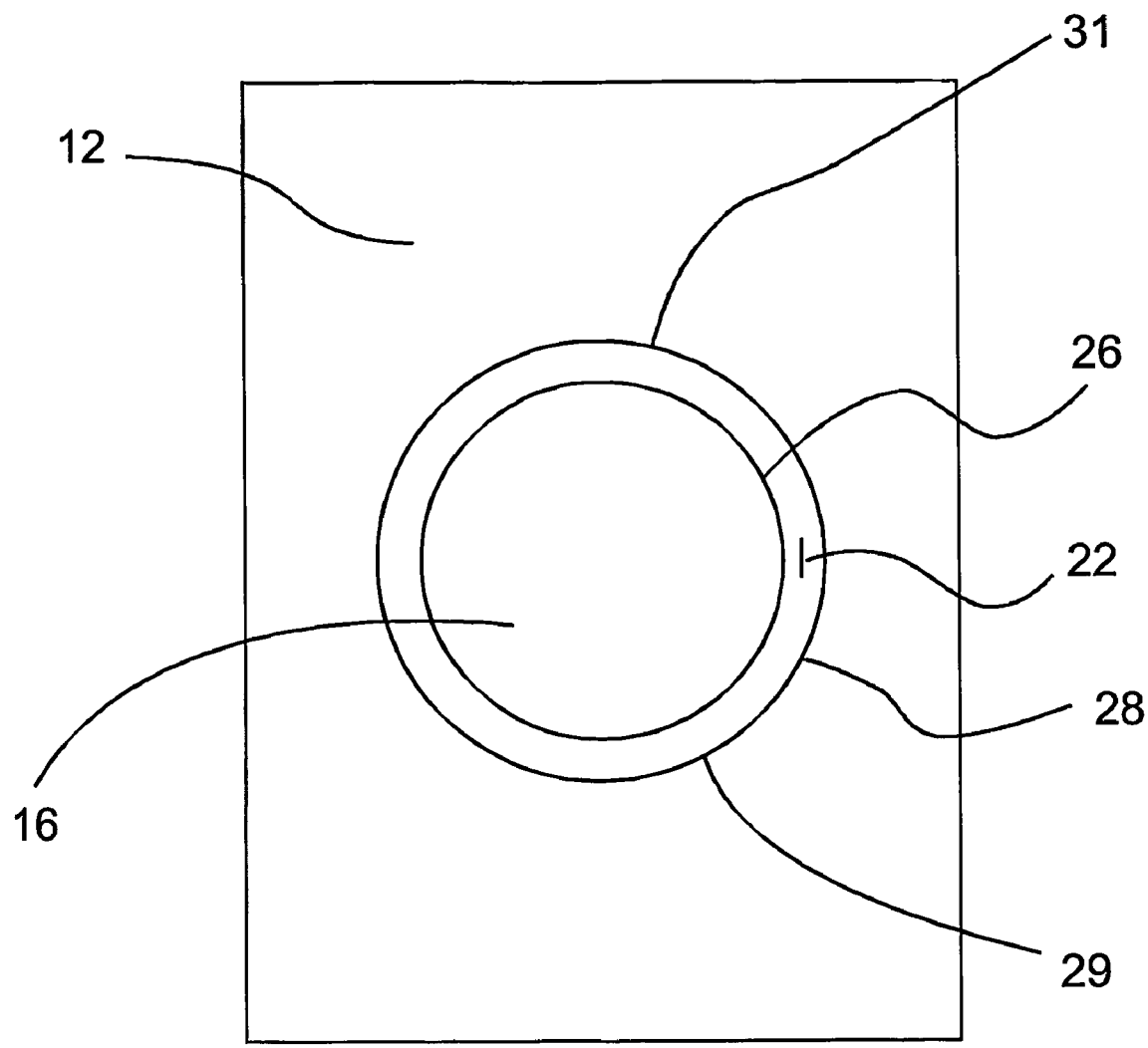
FIG. 13A and FIG. 13B taken together show a second embodiment of a coaxial electrode design with a horizontal operating orientation. A portion of FIG. 13B, as explained below, shows a first embodiment of a coaxial electrode design with a horizontal operating orientation.
Figure 13B:
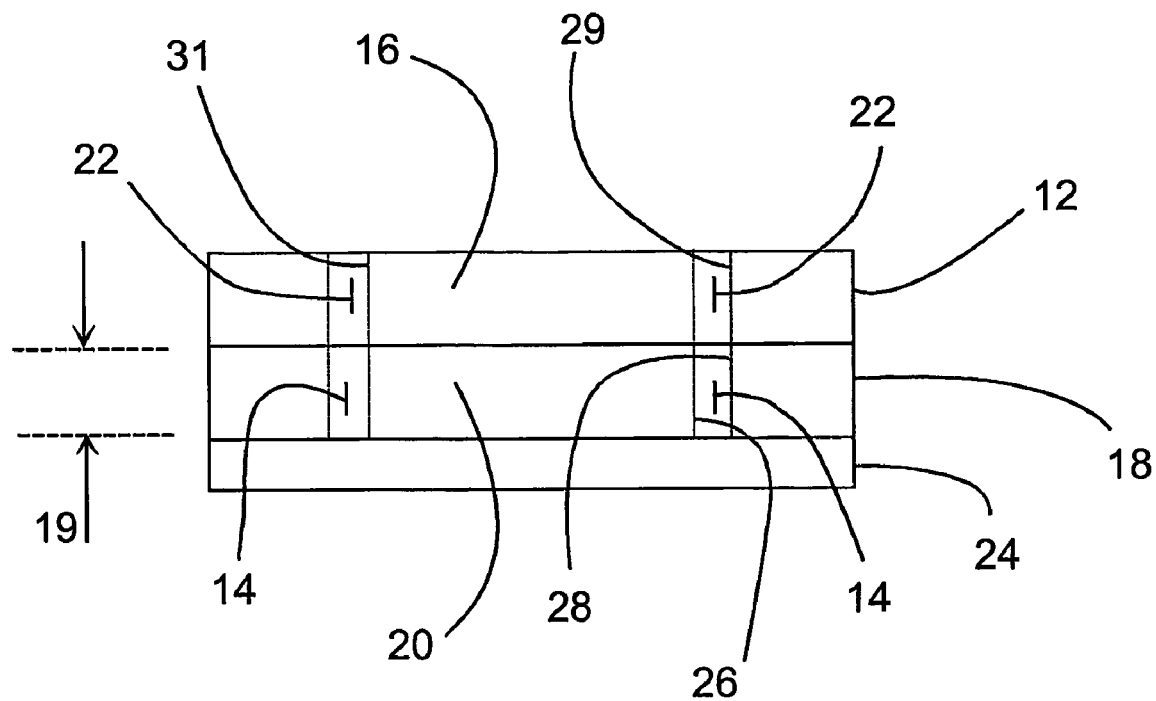

One embodiment of this invention is a coaxial chamber illustrated in FIGS. 13A and 13B. This chamber can be constructed of a square block of conducting material and a square block of non-conducting material. A center electrode of conducting material and an equal height of non-conducting material.

With reference to FIG. 13B, there are shown essentially three layers stacked on each other. The bottommost layer includes the non-conductive base member 24. The middle layer includes the inner electrode 20, the fusion chamber 14, and the inner electrode 20. The topmost layer includes the non-conductive outer electrode cover member 12, the access channel 22, and the non-conductive inner electrode cover member 16.

It is noted that the bottommost layer and the middle layer, taken together, illustrate a first embodiment of the apparatus of the invention. More specifically, the first embodiment of the apparatus is provided for carrying out fusion of biological cells and includes a non-conductive base member 24. A conductive outer electrode 18 is supported on the base member 24, wherein the outer electrode 18 includes a concave outer electrode surface 28 which has an outer electrode radius (r2) and has an electrode height 19. A conductive inner electrode 20 is supported on the base member 24, wherein the inner electrode 20 includes a convex inner electrode-surface 26 which has an inner electrode radius (r1) and has the electrode height 19. The outer electrode surface 28 and the inner electrode surface 26 are spaced apart from each other by a gap which defines a fusion chamber 14.

As discussed above, the first electrode radius (r1), the second electrode radius (r2), and the gap are selected in accordance with a predetermined range of selectable ratios (r1/r2) of the first electrode radius to the second electrode radius, wherein the range of selectable ratios (r1/r2) is from 0.7 to 0.9, wherein a selected gap is limited by the range of selectable ratios (r1/r2), and wherein a determined ratio (r1/r2) of the selectable ratios is based on the selected gap, such that compression between the biological cells 10 and permeability between cell membranes are maximized and temperature rise is minimized for providing cell fusion in the fusion chamber 14.

In accordance with a second embodiment of the invention, also shown in FIG. 13B and in FIG. 13A as well, the topmost layer is fixed to the middle layer. In this respect, the second embodiment of the invention includes all of the bottommost layer, the middle layer, and the topmost layer in FIG. 13B.

More specifically, with respect to the second embodiment of the invention a non-conductive outer electrode cover member 12 is supported by the outer electrode 18. A non-conductive inner electrode cover member 16 is supported by the inner electrode 20, wherein the outer electrode cover member 12 and the inner electrode cover member 16 define an access channel 22, and wherein the access channel 22 is in communication with the fusion chamber 14.

Preferably, the non-conductive outer electrode cover member 12 includes a concave outer cover member surface 29 which has an outer cover member radius. Also, preferably, the non-conductive inner electrode cover member 16 includes a convex inner cover member surface 31 which has an inner cover member radius. Preferably, the outer cover member radius is equal to the outer electrode radius, and the inner cover member radius is equal to the inner electrode radius, whereby the access channel 22 is in registration with the fusion chamber 14.

Non-conductive nylon screws can be used to attach the inner electrode 20 to the base plate 24 and to attach the inner electrode cover member 16 to the inner electrode. Conductive metal screws can be used to attach the outer electrode 18 to the base plate 24 and to attach the outer electrode cover member 12 to the outer electrode 18.

The outer electrode 18 and the inner electrode 20 can be made from stainless steel.

Figure 14:
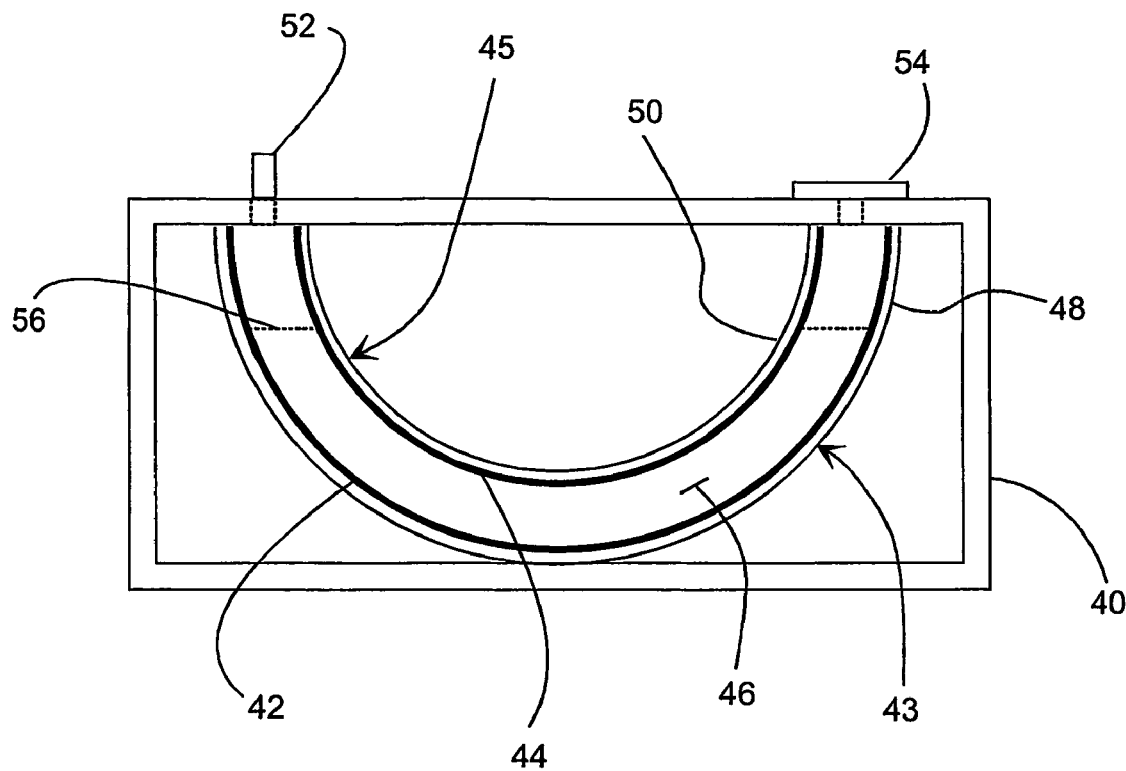
FIG. 14 shows a third embodiment of coaxial electrode design, wherein the third embodiment has a vertical operating orientation.

A third embodiment of a coaxial chamber is illustrated in FIG. 14. Generally, this chamber is a half of a coaxial chamber mounted vertically. When the alignment AC voltage is applied, cell motion will be counter to gravity. This prevents cells from settling to the bottom of the chamber while the waveforms are applied. This chamber may be open or closed with sterile ports and filter relief ports to fill and empty the chamber.

More specifically, this third embodiment of the apparatus includes a non-conductive support member 40. A conductive outer electrode 43 is supported in a horizontal orientation by the support member 40. The outer electrode 43 includes a conductive concave outer electrode surface 42 which has an outer electrode radius (r2) and has an electrode width. A conductive inner electrode 45 is supported in a horizontal orientation by the support member 40 above the outer electrode 43. The inner electrode 45 includes a conductive convex inner electrode surface 44 which has an inner electrode radius (r1) and has the electrode width. A pair of non-conductive vertically oriented end walls are located at ends of the outer electrode 43 and the inner electrode 45. The outer electrode surface 42 and the inner electrode surface 44 are spaced apart from each other by a gap. The gap and the vertically oriented end walls define a fusion chamber 46. The level of cell fusion medium in the fusion chamber 46 is at level 56.

Preferably, the outer electrode 43 includes a non-conductive outer electrode support portion 48 which supports the conductive outer electrode surface 42, and the inner electrode 45 includes a non-conductive inner electrode support portion 50 which supports the conductive inner electrode surface 44. The conductive electrode surfaces 42 and 44 can be a gold film plated onto the respective non-conductive support portions 48 and 50.

In addition, the apparatus can further include an input/output port 52 supported by the support member 40, wherein the input/output port 52 is in communication with the fusion chamber 46.

In addition, the apparatus can further include a filter pressure relief valve 54 supported by the support member 40, wherein the filter pressure relief valve 54 is in communication with the fusion chamber 46.

Preferably, the non-conductive support member 40, the non-conductive outer electrode support portion 48, the non-conductive inner electrode support portion 50, and the non-conductive vertically oriented end walls are formed as an integrated molded plastic unit.

The values of the ratio r1/r2 and the gap are determined by the above method. The chamber may be open or closed. The cells to be fused are placed in a quantity of low conductivity medium and then placed in the gap between the two conducting electrode materials. An AC waveform generator and pulse generator are then connected to the center (inner) conducting electrode and outer conducting electrode.

For electric field generation a voltage waveform generator such as the Cyto Pulse PA-4000/PA-101 computer controlled waveform generator is. After the alignment, compression, fusing and holding waveforms are applied, a cell culture medium is added in the nonconducting volume of the electrode. This culture medium increases the cell viability while the fused cells are recovering.

The apparatus can have large volume research, clinical, and commercial applications. The apparatus can be packed in sterile packaging. Also, the apparatus can be manufactured as single-use disposable units. In all embodiments the volume may be increased by increasing the electrode height. Temperature increase is not a function of electrode height.

While the present invention has been shown in the drawings and fully described above with particularity and detail in connection with what is presently deemed to be the most practical and preferred embodiments of the invention, it will be apparent to those of ordinary skill in the art that many modifications thereof may be made without departing from the principles and concepts set forth herein, including but not limited to, variations in size, materials, shape, form, function and manner of operation assembly and use.

The invention claimed is:

1. An apparatus for carrying out fusion of biological cells, comprising:
    an inner electrode having a first electrode radius (r1) and an electrode height,
    an outer electrode having a second electrode radius (r2) and said electrode height, wherein said inner electrode and said outer electrode are concentric,
    a gap between said inner electrode and said outer electrode, wherein the size of said gap is the difference between said second electrode radius and said first electrode radius, and wherein a cell fusion volume is defined by said electrode height, said gap, said first electrode radius (r1), and said second electrode radius (r2), wherein said first electrode radius, said second electrode radius, and said gap are selected in accordance with a predetermined range of selectable ratios of said first electrode radius to said second electrode radius, wherein said range of selectable ratios is from 0.7 to 0.9, a selected gap limited to a range from 2 to 10 millimeters, and a determined ratio of said selectable ratios based on said selected gap, such that compression between the biological cells and permeability between cell membranes are maximized and temperature rise is minimized for providing cell fusion in said cell fusion volume.

2. The apparatus of claim 1 wherein said cell fusion volume has a volume of greater than one milliliter.

3. The apparatus of claim 1 wherein said ratio of said first electrode radius to said second electrode radius is in a range of 0.75 to 0.9.

4. The apparatus of claim 1 wherein:
    said ratio of said first electrode radius to said second electrode radius is in a range of 0.8 to 0.85, and said gap is in a range of 2 to 10 millimeters.

5. The apparatus of claim 1 wherein:
    said ratio of said first electrode radius to said second electrode radius is 0.83, and
    said gap is 4 millimeters.

6. A method for selecting an inner electrode, an outer electrode, and a gap between the inner electrode and the outer electrode for a cell fusion chamber for fusing biological cells, comprising the steps of:
    determining two of a first electrode radius of the inner electrode, a second electrode radius of the outer electrode, and the gap between the inner electrode and the outer electrode, wherein the gap is within a range from 2 to 10 milliliters,
    setting the ratio (r1/r2) of the first electrode radius to the second electrode radius to a value in a range between 0.7 to 0.9, and
    calculating the third of the first electrode radius of the inner electrode, the second electrode radius of the outer electrode, and the gap between the inner electrode and the outer electrode, based on the set value of the ratio, such that compression between the biological cells and permeability between cell membranes are maximized and temperature rise is minimized for providing cell fusion in the cell fusion chamber.

7. An apparatus for carrying out fusion of biological cells, comprising:
    a non-conductive base member,
    a conductive outer electrode supported on said base member, wherein said outer electrode includes a concave outer electrode surface which has an outer electrode radius (r2) and has an electrode height,
    a conductive inner electrode supported on said base member, wherein said inner electrode includes a convex inner electrode surface which has an inner electrode radius (r1) and has the electrode height, wherein said outer electrode surface and said inner electrode surface are spaced apart from each other by a gap which defines a fusion chamber, a non-conductive outer electrode cover member supported by said outer electrode, and a non-conductive inner electrode cover member supported by said inner electrode, wherein said outer electrode cover member and said inner electrode cover member define an access channel, wherein said access channel is in communication with said fusion chamber, wherein:

said non-conductive outer electrode cover member includes a concave outer cover member surface which has an outer cover member radius, said non-conductive inner electrode cover member includes a convex inner cover member surface which has an inner cover member radius, and said outer cover member radius is equal to said outer electrode radius, and said inner cover member radius is equal to said inner electrode radius, whereby said access channel is in registration with said fusion chamber.

* * * * *